(12) United States Patent
Truckai et al.

(10) Patent No.: US 7,309,849 B2
(45) Date of Patent: Dec. 18, 2007

(54) POLYMER COMPOSITIONS EXHIBITING A PTC PROPERTY AND METHODS OF FABRICATION

(75) Inventors: Csaba Truckai, Saratoga, CA (US); John Shadduck, Tiburon, CA (US)

(73) Assignee: SurgRx, Inc., Redwood City, CA (US)

( * ) Notice: Subject to any disclaimer, the term of this patent is extended or adjusted under 35 U.S.C. 154(b) by 131 days.

(21) Appl. No.: 10/993,210

(22) Filed: Nov. 18, 2004

(65) Prior Publication Data

US 2006/0000823 A1 Jan. 5, 2006

Related U.S. Application Data

(60) Provisional application No. 60/563,424, filed on Apr. 19, 2004, provisional application No. 60/523,567, filed on Nov. 19, 2003.

(51) Int. Cl.
*H05B 3/10* (2006.01)
*H01L 7/10* (2006.01)

(52) U.S. Cl. .................... 219/553; 338/22 R
(58) Field of Classification Search .......... 219/553, 219/552, 538; 338/22 R, 25; *H05B 3/10; H01C 7/10*
See application file for complete search history.

(56) References Cited

U.S. PATENT DOCUMENTS

| | | | |
|---|---|---|---|
| 659,409 | A | 10/1900 | Mosher |
| 1,586,645 | A | 6/1926 | Bierman |
| 1,798,902 | A | 3/1931 | Raney |
| 1,881,250 | A | 10/1932 | Tomlinson |
| 2,031,682 | A | 2/1936 | Wappler et al. |
| 3,651,811 | A | 3/1972 | Hildebrandt et al. |
| 3,685,518 | A | 8/1972 | Beuerle et al. |
| 3,730,188 | A | 5/1973 | Ellman |
| 3,768,482 | A | 10/1973 | Shaw |
| 3,826,263 | A | 7/1974 | Cage et al. |

(Continued)

FOREIGN PATENT DOCUMENTS

EP 341 446 A2 4/1989

(Continued)

OTHER PUBLICATIONS

Corson, S.L., "Two new laparoscopic instruments: Bipolar sterilizing forceps and uterine manipulator," *Medical Instrumentation*, 11(1):7-8 (1977).

(Continued)

*Primary Examiner*—Daniel Robinson
(74) *Attorney, Agent, or Firm*—Townsend and Townsend and Crew LLP

(57) ABSTRACT

Various embodiments of the invention provide polymeric compositions including PTC composites that exhibit highly non-linear PTC effects together with extremely rapid, repeatable switching within a predetermined temperature range. In one embodiment, the polymer composite includes a polymer base material with dispersed conductive particles that have very low densities and very low thermal conductivity properties. The conductive particle component can comprise hollow glass microspheres to provide low mass and low thermal conductivity properties together with a nanoscale conductive cladding of silver or gold. The conductively clad microspheres have a core portion with a bulk density of less than about 2.0 $g/cm^3$ and a mean thermal conductivity of less than about 5.0 W/m-° K.

22 Claims, 5 Drawing Sheets

U.S. PATENT DOCUMENTS

| | | |
|---|---|---|
| 4,092,986 A | 6/1978 | Schneiderman |
| 4,198,957 A | 4/1980 | Cage et al. |
| 4,219,025 A | 8/1980 | Johnson |
| 4,231,371 A | 11/1980 | Lipp |
| 4,232,676 A | 11/1980 | Herczog |
| 4,271,838 A | 6/1981 | Lasner et al. |
| 4,353,371 A | 10/1982 | Cosman |
| 4,370,980 A | 2/1983 | Lottick |
| 4,375,218 A | 3/1983 | DiGeronimo |
| 4,492,231 A | 1/1985 | Auth |
| 4,590,934 A | 5/1986 | Malis et al. |
| 4,608,981 A | 9/1986 | Rothfuss et al. |
| 4,633,874 A | 1/1987 | Chow et al. |
| 4,655,216 A | 4/1987 | Tischer |
| 4,671,274 A | 6/1987 | Sorochenko |
| 4,691,703 A | 9/1987 | Auth et al. |
| 4,763,669 A | 8/1988 | Jaeger |
| 4,785,807 A | 11/1988 | Blanch |
| 4,848,337 A | 7/1989 | Shaw et al. |
| 4,850,353 A | 7/1989 | Stasz et al. |
| 4,887,612 A | 12/1989 | Esser et al. |
| 4,930,494 A | 6/1990 | Takehana et al. |
| 4,940,468 A | 7/1990 | Petillo |
| 4,958,539 A | 9/1990 | Stasz et al. |
| 4,969,885 A | 11/1990 | Farin |
| 4,985,030 A | 1/1991 | Melzer et al. |
| 5,009,656 A | 4/1991 | Reimels |
| 5,057,106 A | 10/1991 | Kasevich et al. |
| 5,057,107 A | 10/1991 | Parins et al. |
| 5,085,659 A | 2/1992 | Rydell |
| 5,104,025 A | 4/1992 | Main et al. |
| 5,122,137 A | 6/1992 | Lennox |
| 5,147,356 A | 9/1992 | Bhatta |
| 5,147,357 A | 9/1992 | Rose et al. |
| 5,151,102 A | 9/1992 | Kamiyama et al. |
| 5,190,541 A | 3/1993 | Abele et al. |
| 5,201,900 A | 4/1993 | Nardella |
| 5,207,691 A | 5/1993 | Nardella |
| 5,258,006 A | 11/1993 | Rydell et al. |
| 5,267,998 A | 12/1993 | Hagen |
| 5,269,780 A | 12/1993 | Roos |
| 5,280,263 A * | 1/1994 | Sugaya .................... 338/22 R |
| 5,290,286 A | 3/1994 | Parins |
| 5,306,280 A | 4/1994 | Bregen et al. |
| 5,308,311 A | 5/1994 | Eggers et al. |
| 5,324,289 A | 6/1994 | Eggers |
| 5,336,221 A | 8/1994 | Anderson |
| 5,360,428 A | 11/1994 | Hutchinson, Jr. |
| 5,364,389 A | 11/1994 | Anderson |
| 5,389,098 A | 2/1995 | Tsuruta et al. |
| 5,403,312 A | 4/1995 | Yates et al. |
| 5,417,687 A | 5/1995 | Nardella et al. |
| 5,443,463 A | 8/1995 | Stern et al. |
| 5,445,638 A | 8/1995 | Rydell et al. |
| 5,451,224 A | 9/1995 | Goble et al. |
| 5,458,598 A | 10/1995 | Feinberg et al. |
| 5,480,397 A | 1/1996 | Eggers et al. |
| 5,480,398 A | 1/1996 | Eggers |
| 5,507,106 A | 4/1996 | Fox |
| 5,531,744 A | 7/1996 | Nardella et al. |
| 5,571,153 A | 11/1996 | Wallsten |
| 5,573,535 A | 11/1996 | Viklund |
| 5,593,406 A | 1/1997 | Eggers et al. |
| 5,603,875 A | 2/1997 | Giller et al. |
| 5,611,798 A | 3/1997 | Eggers |
| 5,624,452 A | 4/1997 | Yates |
| 5,674,220 A | 10/1997 | Fox et al. |
| 5,693,051 A | 12/1997 | Schulze et al. |
| 5,716,366 A | 2/1998 | Yates |
| 5,735,848 A | 4/1998 | Yates et al. |
| 5,755,717 A | 5/1998 | Yates et al. |
| 5,766,166 A | 6/1998 | Hooven |
| 5,776,130 A | 7/1998 | Buysse et al. |
| 5,782,301 A * | 7/1998 | Neuroth et al. .............. 166/302 |
| 5,797,938 A | 8/1998 | Paraschal et al. |
| 5,800,449 A | 9/1998 | Wales |
| 5,807,392 A | 9/1998 | Eggers |
| 5,833,690 A | 11/1998 | Yates et al. |
| 5,836,874 A | 11/1998 | Swanson et al. |
| 5,849,011 A | 12/1998 | Jones et al. |
| 5,891,142 A | 4/1999 | Eggers et al. |
| 5,911,719 A | 6/1999 | Eggers |
| 5,947,984 A | 9/1999 | Whipple |
| 6,019,758 A | 2/2000 | Slater |
| 6,030,384 A | 2/2000 | Nezhat |
| 6,039,733 A | 3/2000 | Buysse et al. |
| 6,074,389 A | 6/2000 | Levine et al. |
| 6,086,586 A | 7/2000 | Hooven |
| 6,106,558 A | 8/2000 | Picha |
| 6,107,699 A | 8/2000 | Swanson |
| 6,113,598 A | 9/2000 | Baker |
| 6,132,426 A | 10/2000 | Kroll |
| 6,139,508 A | 10/2000 | Simpson et al. |
| 6,143,207 A | 11/2000 | Yamada et al. |
| 6,152,923 A | 11/2000 | Ryan |
| 6,162,220 A | 12/2000 | Nezhat |
| 6,174,309 B1 | 1/2001 | Wrublewski et al. |
| 6,176,857 B1 | 1/2001 | Ashley |
| 6,179,834 B1 | 1/2001 | Buysse et al. |
| 6,179,835 B1 | 1/2001 | Panescu et al. |
| 6,179,837 B1 | 1/2001 | Hooven |
| 6,187,003 B1 | 2/2001 | Buysse et al. |
| 6,190,386 B1 | 2/2001 | Rydell |
| 6,193,709 B1 | 2/2001 | Miyawaki et al. |
| 6,270,497 B1 | 8/2001 | Sekino et al. |
| 6,273,887 B1 | 8/2001 | Yamauchi et al. |
| 6,277,117 B1 | 8/2001 | Tetzlaff et al. |
| 6,281,263 B1 | 8/2001 | Evans et al. |
| 6,296,640 B1 | 10/2001 | Wampler et al. |
| 6,298,550 B1 | 10/2001 | Kirwan, Jr. |
| 6,328,703 B1 | 12/2001 | Murakami |
| 6,334,861 B1 | 1/2002 | Chandler et al. |
| 6,350,264 B1 | 2/2002 | Hooven |
| 6,352,536 B1 | 3/2002 | Buysse et al. |
| 6,398,779 B1 | 6/2002 | Buysse et al. |
| 6,409,725 B1 | 6/2002 | Khandkar et al. |
| 6,451,018 B1 | 9/2002 | Lands et al. |
| 6,458,127 B1 | 10/2002 | Truckai et al. |
| 6,458,128 B1 | 10/2002 | Schulze |
| 6,458,130 B1 | 10/2002 | Frazier et al. |
| 6,464,704 B2 | 10/2002 | Schmaltz |
| 6,468,275 B1 | 10/2002 | Wampler et al. |
| 6,485,436 B1 | 11/2002 | Truckai et al. |
| 6,500,176 B1 | 12/2002 | Truckai et al. |
| 6,511,480 B1 | 1/2003 | Tetzlaff et al. |
| 6,527,767 B2 | 3/2003 | Wang et al. |
| 6,533,784 B2 | 3/2003 | Truckai et al. |
| 6,554,829 B2 | 4/2003 | Schulze et al. |
| 6,575,968 B1 | 6/2003 | Eggers et al. |
| 6,585,735 B1 | 7/2003 | Frazier et al. |
| 6,607,679 B2 * | 8/2003 | Handa et al. ................ 252/513 |
| 6,632,193 B1 | 10/2003 | Davison et al. |
| 6,652,521 B2 | 11/2003 | Schulze |
| 7,049,926 B2 * | 5/2006 | Shrier et al. .................. 338/21 |
| 2002/0052599 A1 | 5/2002 | Goble |
| 2002/0115997 A1 | 8/2002 | Truckai et al. |
| 2002/0120266 A1 | 8/2002 | Truckai et al. |
| 2002/0130757 A1* | 9/2002 | Huang et al. ............. 338/22 R |
| 2002/0169392 A1 | 11/2002 | Truckai et al. |
| 2002/0177848 A1 | 11/2002 | Truckai et al. |
| 2003/0018327 A1 | 1/2003 | Truckai et al. |
| 2003/0050635 A1 | 3/2003 | Truckai et al. |
| 2003/0055417 A1 | 3/2003 | Truckai et al. |
| 2003/0069579 A1 | 4/2003 | Truckai et al. |

| | | | |
|---|---|---|---|
| 2003/0078573 A1 | 4/2003 | Truckai et al. | |
| 2003/0078577 A1 | 4/2003 | Truckai et al. | |
| 2003/0078578 A1 | 4/2003 | Truckai et al. | |
| 2003/0114851 A1 | 6/2003 | Truckai et al. | |
| 2003/0125727 A1 | 7/2003 | Truckai et al. | |
| 2003/0139741 A1 | 7/2003 | Goble et al. | |
| 2003/0144652 A1 | 7/2003 | Baker et al. | |

FOREIGN PATENT DOCUMENTS

| | | | |
|---|---|---|---|
| EP | 517 244 B1 | 3/1996 | |
| EP | 518 230 B1 | 5/1996 | |
| FR | 2536924 A1 | 6/1984 | |
| FR | 2647683 A1 | 12/1990 | |
| GB | 2037167 A | 7/1980 | |
| GB | 2066104 A | 7/1981 | |
| GB | 2133290 A | 7/1984 | |
| GB | 2161082 A | 1/1986 | |
| SU | 342617 | 1/1973 | |
| SU | 575103 | 10/1977 | |
| WO | WO 93/08754 A1 | 5/1993 | |
| WO | WO 94/24949 A1 | 11/1994 | |
| WO | WO 94/24951 A1 | 11/1994 | |
| WO | WO 00/09190 A1 | 2/2000 | |

OTHER PUBLICATIONS

Burton, J.D.K., "New Inventions," *The Lancet*, pp. 650-651 (1959).

Nardella, P.C., "Radio Frequency Energy and Impedance Feedback," *Proc. SPIE, Catheter-Based Sensing and Imaging Technology*, 1068: 42-48 (1989).

Pacific Silk, "Designing with Silicon Synthetic Rubber" brochure, downloaded on Nov. 1, 2004, <<http//www.pacificsilk.com>>, 12 pages total.

Vallfors et al., "Automatically controlled bipolar electrocoagulation—'COA-COMP'," *Neurosurg Rev.*, 187-190 (1984).

\* cited by examiner

L
POLYMER COMPOSITIONS EXHIBITING A PTC PROPERTY AND METHODS OF FABRICATION

CROSS-REFERENCES TO RELATED APPLICATIONS

This application claims the benefit of priority of U.S. Provisional Patent Application Ser. No. 60/563,424, filed Apr. 19, 2004, entitled Electrosurgical Instrument With PTC Sensing Surface and U.S. Provisional Patent Application Ser. No. 60/523,567, filed Nov. 19, 2003, entitled Electrosurgical Instrument and Method of Use, both of which are fully incorporated herein by reference. This application is also related to U.S. patent application Ser. No. 10/032,867, filed Oct. 22, 2001, entitled Electrosurgical Jaw Structure for Controlled Energy Delivery and concurrently filed U.S. patent application Ser. No. 10/308,362 both of which are fully incorporated herein by reference.

BACKGROUND OF THE INVENTION

Field of the Invention

Embodiments of the invention relate to polymeric compositions that exhibit highly non-linear positive temperature coefficient of resistance properties (hereafter, simply PTC) and electronic and electrosurgical devices made from such compositions. Various embodiments also relate to methods of fabricating such PTC compositions, PTC devices, often referred to as PTC thermistors, are well known in electronic industries and are used as low power circuit protectors, as well as for thermal sensors and as constant temperature heaters. FIG. 1A is an exploded view of a prior art current-limiting device or thermistor 5 that has a polymeric PTC material 10 sandwiched between foil electrodes (12a and 12b) and packaged within an insulator 14 (phantom view). FIG. 1B is a schematic view of a prior art current-limiting device or thermistor 5 in a circuit diagram showing that heating of the PTC material can limit current flow to the load 16. FIG. 1C is a schematic view of a PTC device 25 that consists of a constant temperature heating element for heating subject material 26 in contact with the device. In other words, the device of FIG. 1C comprises a PTC heater material that conducts heat to the engaged subject article 26.

Polymeric PTC material consists of a crystalline or semi-crystalline polymer (e.g., polyethylene) that carries a dispersed filler of conductive particles, such as carbon powder or nickel particles. In use, a polymeric PTC material exhibits temperature-induced changes in the base polymer to alter electrical resistance of the polymer-particle composite. In a low temperature state, the crystalline structure of the base polymer causes dense packing of the conductive particles (i.e., carbon) into its crystalline boundaries so that the particles are in close proximity and allow current to flow through the PTC material via these carbon "chains". When the PTC material is at a low temperature, numerous carbon chains form the conductive paths through the material. When the PTC material is heated to a selected level, or an over-current causes $I^2R$ heating (Joule heating), the polymer base material thus will be elevated in temperature until it exceeds a phase transformation temperature. As the polymer passes through this phase transformation temperature, the crystalline structure changes to an amorphous state. The amorphous state causes the conductive particles to move apart from each other until the carbon chains are disrupted and no longer conduct current. Thus, the resistance of the PTC material increases sharply. In general, the temperature at which the base polymer transitions to its amorphous state and affects conductivity is called its switching temperature $T_S$.

As long as the base polymer of the PTC material stays above its $T_S$, whether from external heating or from an overcurrent, the high resistance state will remain. Reversing the phase transformation allows the conductive particle chains to reform as the polymer re-crystallizes to thereby restore multiple current paths (e.g., low resistance) through the PTC material.

Conductive polymer PTC compositions and their use as circuit protection devices are well known in the industry. For example, U.S. Pat. No. 4,237,441 (Van Konynenburg et al.), U.S. Pat. No. 4,304,987 (Van Konynenburg), U.S. Pat. No. 4,545,926 (Fouts, Jr. et al.), U.S. Pat. No. 4,849,133 (Yoshida et al.), U.S. Pat. No. 4,910,389 (Sherman et al.), U.S. Pat. No. 5,106,538 (Barma et al.), and U.S. Pat. No. 5,880,668 (Hall) and EP-730 282 A2 (Unitika) disclose PTC compositions that comprise thermoplastic crystalline polymers with carbon particles or other conductive particles dispersed therein. The disclosure of each one of these references is incorporated herein by this reference.

PTC devices most often only play a passive role in an electronic circuit, and "switch" when a voltage spike overheats the polymeric material thereby causing its resistance also to spike. However, these devices do not consider the problem of rapid switching from a conductive to a resistive mode. There is a need for conductive polymer PTC compositions such as PTC composites which can switch in an extremely rapid, repetitive manner from a conductive to a resistive mode. There is also a need for PTC materials which have pixelated (localizable) switching across a surface of the PTC composition.

BRIEF SUMMARY OF THE INVENTION

Embodiments of the invention provide various polymer compositions exhibiting positive temperature coefficient of resistance (PTC) properties. In many embodiments, the invention provides a conductive polymer composition comprising a matrix of at least one polymer component and a plurality of conductively clad elements dispersed within the at least one polymer component. In one embodiment, the plurality of conductively clad elements can comprise at least about 20% by volume of the composition and in another embodiment, can comprise 40% by volume of the composition. The elements include a core portion and clad or cladding portion. In one embodiment, the core portions of the plurality of elements have a bulk density of less than about 2.0 g/cm³. In other embodiments, the bulk density of the core portions can be less than about 1.0 g/cm³ or even about 0.5 g/cm³.

Embodiments of the invention also provide a conductive polymer composition comprising a polymeric PTC composite that exhibits highly nonlinear PTC effects together with extremely rapid, repeatable switching at a selected switching temperature. In an exemplary embodiment, the polymer composite comprises a polymer base material with a plurality of dispersed conductive elements that have very low densities and very low thermal conductivity properties. The conductive particle component can comprise core-shell elements such as hollow glass microspheres to provide low mass and low thermal conductivity properties together with a nanoscale conductive coating. In preferred embodiments, the polymeric PTC composites have a plurality of conductively clad elements which have a core portion with a bulk density of less than about 2.0 g/cm$^3$ and a thermal conductivity of less than about 5.0 W/m-° K. The proportion of elements having such mass and thermal properties can range from 1 to 100% with specific embodiments of 10, 25, 50, 75 and 95%. In preferred embodiments, a majority of the elements can have such properties. Also, the plurality of the core portion can have mean values for thermal conductivity which are less than about 5.0 W/m-° K.

Embodiments of the invention also provide polymer PTC composites that have selectable material and/or electrical properties suitable for various electrical applications and/or devices. One embodiment provides a PTC composite having a highly stable current-limiting properties and is capable of repeated cycling between an initial quiescent resistance and its operating resistance or switching range. Another embodiment provides a polymer PTC composites having an enhanced $I_{HOLD}$ property. This is the maximum current the composition will hold for a selected time interval at a predetermined temperature. In related embodiments, the invention provides a polymeric PTC composite suitable for fabrication of thermistors for very rapid repetitive use such as is required in telecommunications devices and equipment. Other embodiments provide a polymer PTC composite having one or more of the following properties: i) a greatly reduced $R_{IL}$ property (this is its initial low resistance level in a quiescent state); ii) an increased $I_{MAX}$ property (this is the maximum current the material withstands without damage); iii) a current-limiting material that can be configured to disallows I$^2$R (Joule) heating thereof; and iv) a material that can spatially modulate current flow across its surface for use in electrosurgical applications such as in electrosurgical devices including one or more electrosurgical energy delivery surfaces.

Other embodiment provide a PTC device comprising a PTC element comprising a conductive polymer composition exhibiting a PTC property and an electrode electrically coupled to the PTC element. The electrode is configured to be coupled to an electrical voltage source or power source. In various embodiments, the device can be configured as a thermistor, a sensor, a current limiting device, a heater or an electrosurgical device. For electrosurgical applications, the power source can be a radio frequency power source known in the art such as an Rf generator.

Another embodiments provides a method of making a conductive polymer composition exhibiting a PTC property such as a "nonlinear" PTC effect. The method comprises providing a thermoplastic polymeric base material and a volume of dispersible conductively clad elements wherein the core portions of the elements in the volume have a mean thermal conductivity of less than about 5.0 W/m-° K. The elements are then mixed in the polymeric base material. The formulated conductive polymers composition can then be processed or machined to make a PTC device or article. In one embodiment, the formulated conductive polymer composition can be pressed into sheet material used to manufacture thermistors, thermal sensors, combination thermal sensing and current-conducting devices for electrosurgical energy-delivery surfaces, and constant temperature heating devices.

BRIEF DESCRIPTION OF THE DRAWINGS

The accompanying drawings are included to provide a further understanding of embodiments of the invention and are incorporated in and constitute a part of this disclosure.

DESCRIPTION OF THE PREFERRED EMBODIMENTS

Figure 1A:
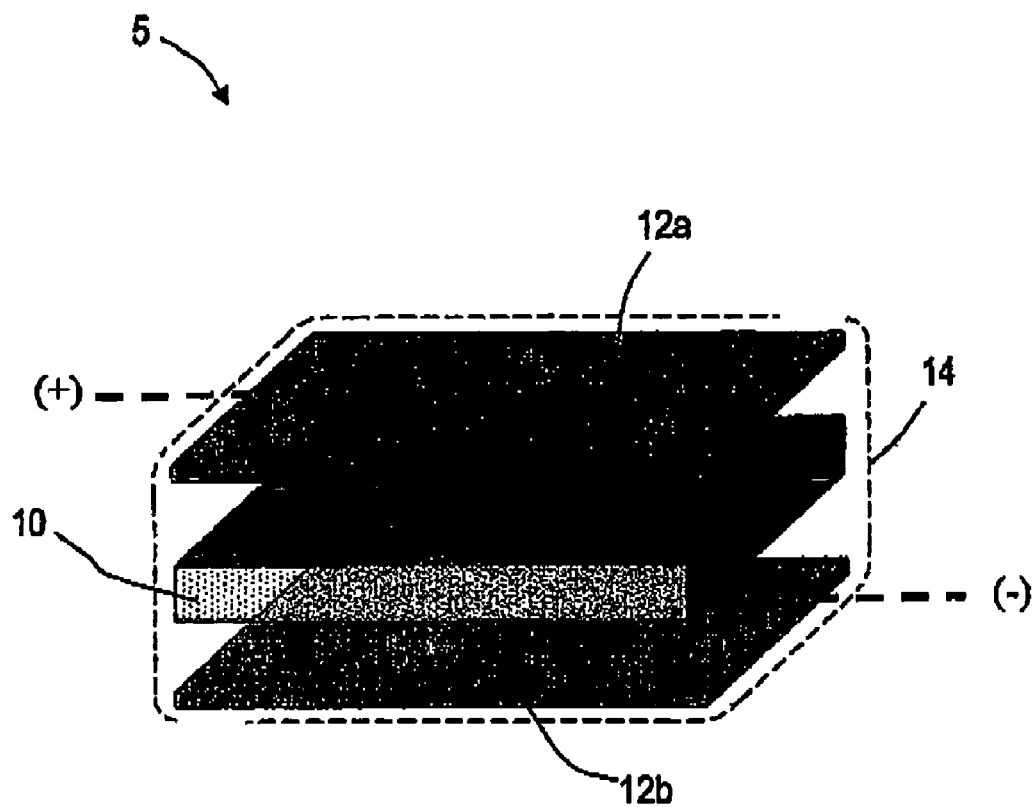
FIG. 1A is an exploded schematic view of a prior art current-limiting device with a polymeric PTC body sandwiched between first and second electrodes.

1. Operational principles of polymer PTC composites. Various embodiments of the invention provide polymeric compositions that exhibit positive temperature coefficient of resistance (PTC) effects, and articles, devices and systems made there from. Describing a material as having a positive temperature coefficient of resistance (PTC) simply means that the resistance of the material increases as temperature increases. Many metal-like materials exhibit electrical conduction that has a slight positive temperature coefficient of resistance. (Materials that conduct like metals have the lowest resistivity of all non-superconducting materials, wherein resistivity generally falls in the range of 1-100 μΩ-cm.). In such metal-like materials, the PTC's variable resistance effect is characterized by a gradual increase in resistance that is linearly proportional to temperature—that is, a linear PTC effect.

A "nonlinear" PTC effect is exhibited by certain types of polymer matrices that are doped with conductive particles. These polymer PTC compositions have a base polymer that undergoes a phase change or glass transition temperature $T_G$ wherein the PTC composition has a resistance that increases sharply over a narrow temperature range (see FIG. 2). This invention is related only to fabrication and use of PTC compositions that exhibit highly non-linear PTC curves.

For ease of discussion, the following definitions are provided for terms relating to operational characteristics of polymeric PTC compositions:

$T_S$: Switching temperature: temperature at which composition exhibits very large nonlinear PTC effect; that is it will "trip" to very high current-limiting resistivity from low quiescent resistivity;

$T_G$: Temperature of glass transition of polymeric base material to rubbery state;

$T_M$: Temperature at which crystalline material transitions to flowable material;

$I_{Hold}$: Hold current: maximum current the composition will sustain for a selected time interval at a certain temperature (e.g., 20° C.);

$I_{Trip}$: Trip current: minimum current that will cause the composition to reach its switching range to become non-conductive at a certain temperature (e.g., 20° C.);

$V_{Max}$: Maximum voltage: maximum voltage the PTC composition withstands without damage;

$I_{Max}$: Maximum current: maximum current the PTC composition withstands without damage;

$R_{IL}$: Minimum resistance of the PTC composition in an initial quiescent state;

$R_{AT}$: Maximum resistance in non-tripped state after cycling between quiescent and operational states; and P_DMax: Power dissipated from the PTC composition when tripped at its switching range.

A discussion will now be presented of the properties of embodiments of the conductive polymer compositions described herein as well as the components of those compositions. In many embodiments, the conductive polymer composition will comprise a base polymer and conductive elements dispersed in the base polymer. When describing properties of the base polymer of a PTC composition, it is useful to further explain the terms glass transition temperature ($T_G$) and melting temperature ($T_M$). A glass transition temperature is not the same as a melting temperature. A transition at $T_M$ occurs in crystalline polymers when the polymer chains fall out of their crystalline phase, and become a disordered deformable or flowable media. A glass transition at $T_G$ is a transition which occurs in amorphous polymers (i.e., polymers whose chains are not arranged in ordered crystals). A glass transition temperature ($T_G$) in a crystalline polymer is herein defined loosely as a temperature point where the polymer experiences a significant change in properties-such as a large change in Young's modulus (also known as modulus of elasticity). The $T_G$ is the temperature at which the polymer structure turns "rubbery" upon heating and "glassy" upon cooling. Crystalline polymers also go through a stage of becoming leathery before becoming rubbery. There is a loss of stiffness (e.g., decreased modulus of elasticity) in both of these stages. Such crystalline polymers or domains thereof have a sharp, defined melting point $T_M$. In contrast, an amorphous polymer is structural below $T_G$ and transitions from being stiff to flowable ($T_M$) over a wide temperature range.

The temperature-induced variable resistance of a polymer PTC composition when used in a prior art current-limiting application is based on an overall energy balance—and can be described by Equation (1) below. It is useful to describe the basic thermal/resistance properties of a PTC device comprising a polymeric PTC composition, to thereafter explain how (i) highly non-linear PTC effects and (ii) rapid switching are achieved in the novel polymeric materials of embodiments of the invention.

$$mC_p(\Delta T/\Delta t)=I^2R-U(T-T_a) \quad (1)$$

Wherein:

m=mass of the PTC composition $C_p$=specific heat capacity of the PTC composition (at a constant pressure)

ΔT=change in temperature of the PTC composition

Δt=change in time

I=current flowing through the PTC composition

R=resistance of the PTC composition

U=overall heat-transfer coefficient

T=temperature of the PTC composition $T_a$=ambient temperature

In equation (1) above, the current flowing through the PTC composition generates heat at a rate equal to $I^2R$. All or some of this heat can be subtracted by interaction with the environment at a rate described by the term $U(T-T_a)$, depending on how the device or composition is configured for interaction with the environment. This equation accounts for losses due to one or more of convection, conduction and radiation. Any heat not subtracted by environmental interaction raises the temperature of the PTC composition/device at a rate described by the term:

$$mC_p(\Delta T/\Delta t) \quad (2)$$

To keep Equation (1) as simple as possible, it is assumed that there is a uniform temperature across the polymeric PTC composition.

If the heat generated by the polymeric PTC composition and the heat subtracted to the operating environment are in balance, T/t goes to zero, and Equation (1) can be rewritten as:

$$I^2R=U(T-T_a) \quad (3)$$

Figure 2:
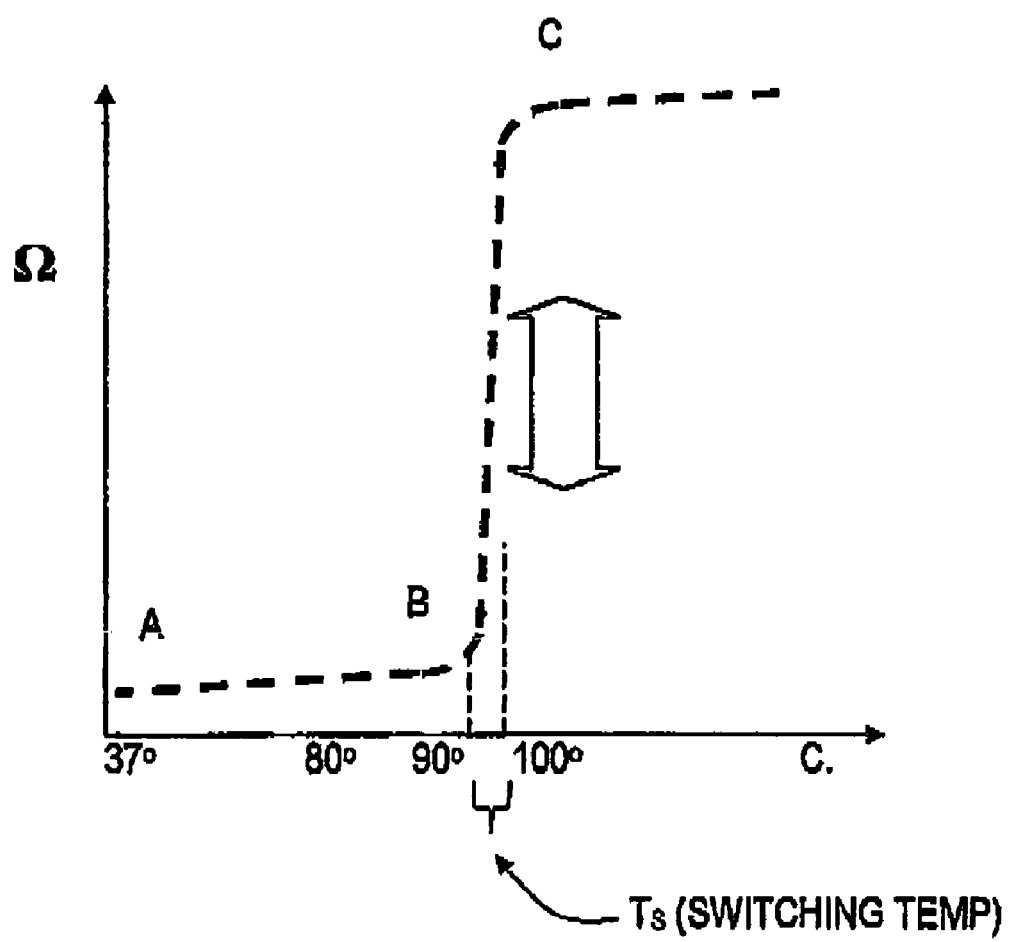
FIG. 2 is an exemplary temperature-resistance curve of a polymeric PTC composition.

Under certain operating conditions, the heat generated by the PTC composition/device and the heat lost by the PTC composition/device to the environment can be in balance at a relatively low temperature—for example, Point A shown in FIG. 2. If the current flow (I) through the PTC composition increases and the ambient temperature remains constant, the heat generated by the PTC composition increases, and the temperature of the PTC composition also increases. But if the increase in current is not too large, all the generated heat can be lost to the environment, and the PTC composition will stabilize according to Equation (3) at a higher temperature, such as Point B in FIG. 2.

If the ambient temperature outside the PTC composition/device, or the temperature of an object engaged by the PTC composition, increases instead of the current, the PTC composition will stabilize according to Equation (3) at a slightly higher temperature (possibly again at Point B in FIG. 2). Point B in FIG. 2 can also be reached as a result of an increase in current (I) and an increase in ambient temperature. Further increases in either or both of these conditions will cause the PTC composition to reach a temperature $T_S$ at which the resistance rapidly increases (e.g., from Point B to Point C in FIG. 2).

Any further increase in current or ambient temperature will cause the PTC composition/device to generate heat at a rate greater than the rate at which heat can be lost to the environment, causing the PTC composition/device to heat up rapidly. At this stage, large increases in resistance occur with small changes in temperature. In FIG. 2, this occurs between Points B and C, and this vertical or "square" portion of the curve defines the operating region of the PTC composition in its tripped state. The large change in resistance causes a corresponding decrease in current flow in a circuit including or otherwise electrically coupled to the PTC composition/device.

Because the temperature change between Points B and C in FIG. 2 is very small, the term $(T-T_a)$ in Equation (3) can be replaced by the constant $(T_S-T_a)$, where $T_S$ is the operating (current-limiting) temperature of the device. Then Equation (1) can be rewritten as:

$$I^2R=V^2/R=U(T_S-T_a) \quad (4)$$

Because U and $(T_S-T_a)$ are now both constants, Equation (4) reduces to $I^2R$=constant; that is, the device now operates in a constant power state. Expressing this constant power as $V^2/R$ emphasizes that, in the tripped state, the resistance of the PTC composition is proportional to the square of the applied voltage. This relation holds until the composition/device resistance reaches the upper "square" region of the curve (Point C in FIG. 2).

For a PTC composition that has tripped, as long as the applied voltage is high enough for the resulting $V^2/R$ to supply the $U(T_S-T_a)$ loss, the PTC composition will remain in the tripped state; that is, the PTC composition will remain substantially non-conductive. When the voltage is decreased to the point at which the $U(T_S-T_a)$ loss can no longer be supplied, the PTC composition will "reset" or return to its quiescent base resistance.

Figure 1B:
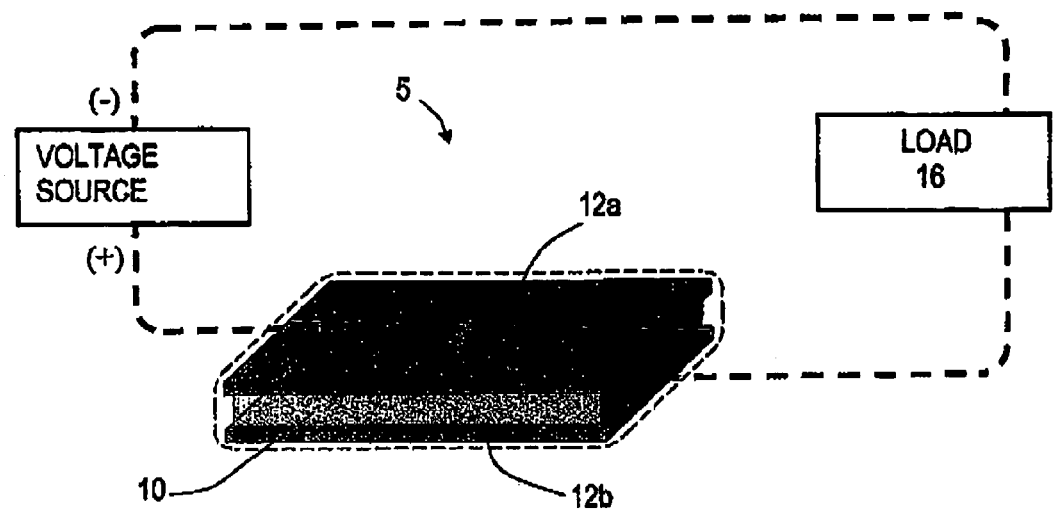
FIG. 1B is a schematic view of a prior art current-limiting device or thermistor in a circuit diagram.
Figure 1C:
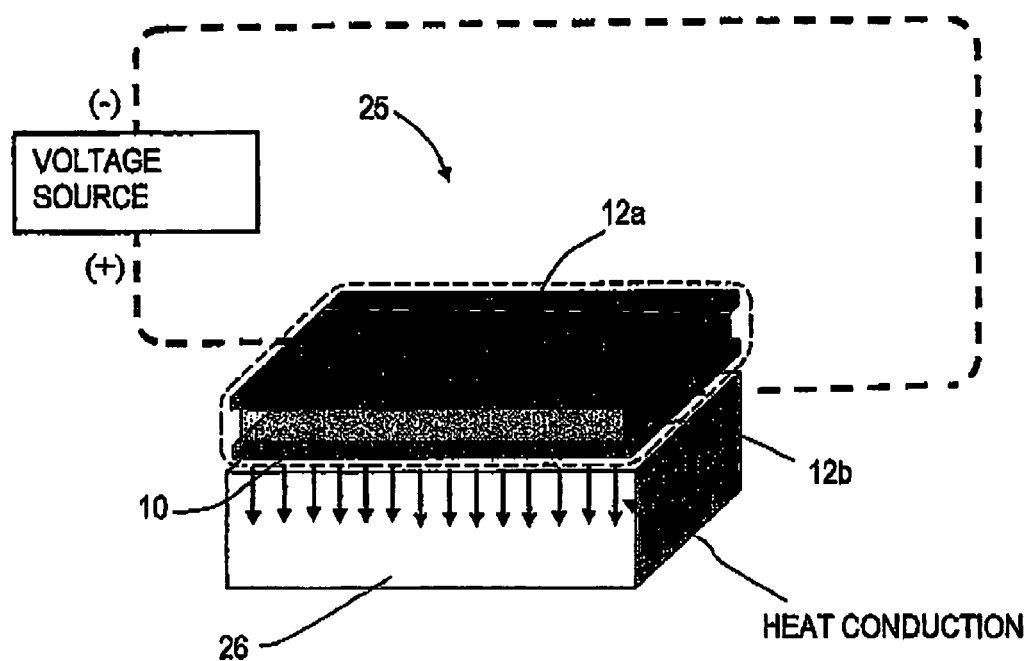
FIG. 1C is a schematic view of a prior art constant temperature heating device in a circuit diagram.

In the context of FIGS. 1B and 1C, it can be understood how the above Equations describe the operation of a PTC composition in a current-limiting device (see cf. FIG. 1B) or a constant temperature heating device (see cf. FIG. 1C).

Various embodiments of the invention provide polymeric PTC compositions including PTC composites that allow for a very rapid bi-directional switching (e.g., a small Δt) between Points B and C along the resistance-temperature curve of FIG. 2 (indicated by arrow). Embodiments of the invention also provide a polymeric PTC composition that exhibits a resistance-temperature curve with a high degree of "squareness" at its $T_S$ (see FIG. 2). That is, the embodiment of the PTC composition will plot an exceedingly rapid nonlinear PTC effect (e.g., a rapid increase in resistivity) in the range of a selected switching temperature $T_S$. A vertical curve at $T_S$ means that the change from a base quiescent $R_{IL}$ resistance to a maximum current-limiting resistance occurs over a very small temperature range.

From the following equation, it can be understood that switching time can be effectively reduced by altering the mass of the PTC composition. The switching time can generally be represented by equation (5):

$$\Delta t = mC_p(T_S - T_a)/I^2R \text{ (i.e., power applied)} \tag{5}$$

By controlling one or more variables from equation 5, various embodiments of the invention provide conductive polymer compositions which have one or both of reduced switching time and/or a square resistance-temperature curve. In particular embodiments, these properties can be achieved by configuring the polymer matrix to have a dispersed conductive component which has a very low mass and density (e.g., cf. m in Equation (5)—and also comprises a substantial percentage of the volume of the PTC body or manufactured article. An exemplary embodiment of a conductive polymer composition/polymer composite which provides a greatly increased switching speed utilizes thermally insulative, low mass, yet electrically conductive dispersed nano- or microspheres. It has also been found that embodiments of such polymer composites can provide a greatly improved $I_{Hold}$ property—the maximum current the composition will hold for a selected time interval at a predetermined temperature.

It has also been found that the embodiments of the above described polymer composite provides very low $R_{IL}$ property. This is the material's minimum resistance in its initial quiescent state. At the same time, the polymer with the thermally insulative, low mass conductive particles provides for an increased $I_{Max}$ property. This is the maximum current the PTC composition can withstand without damage.

In various embodiments, one or more desired PTC properties, e.g., reduced switching time, can also be achieved by providing a dispersed conductive component that has a substantially low specific heat capacity (see $C_p$ in Equations (1) and (2)). As can be seen from Equation 5, low specific heat capacity serves to reduce switching time. The specific heat capacity (also called specific heat) is the amount of heat required to change a unit mass (or unit quantity, such as a mole) of a substance by one degree in temperature, and therefore, has units of energy per mass per degree (or energy per number of moles per degree).

Figure 3:
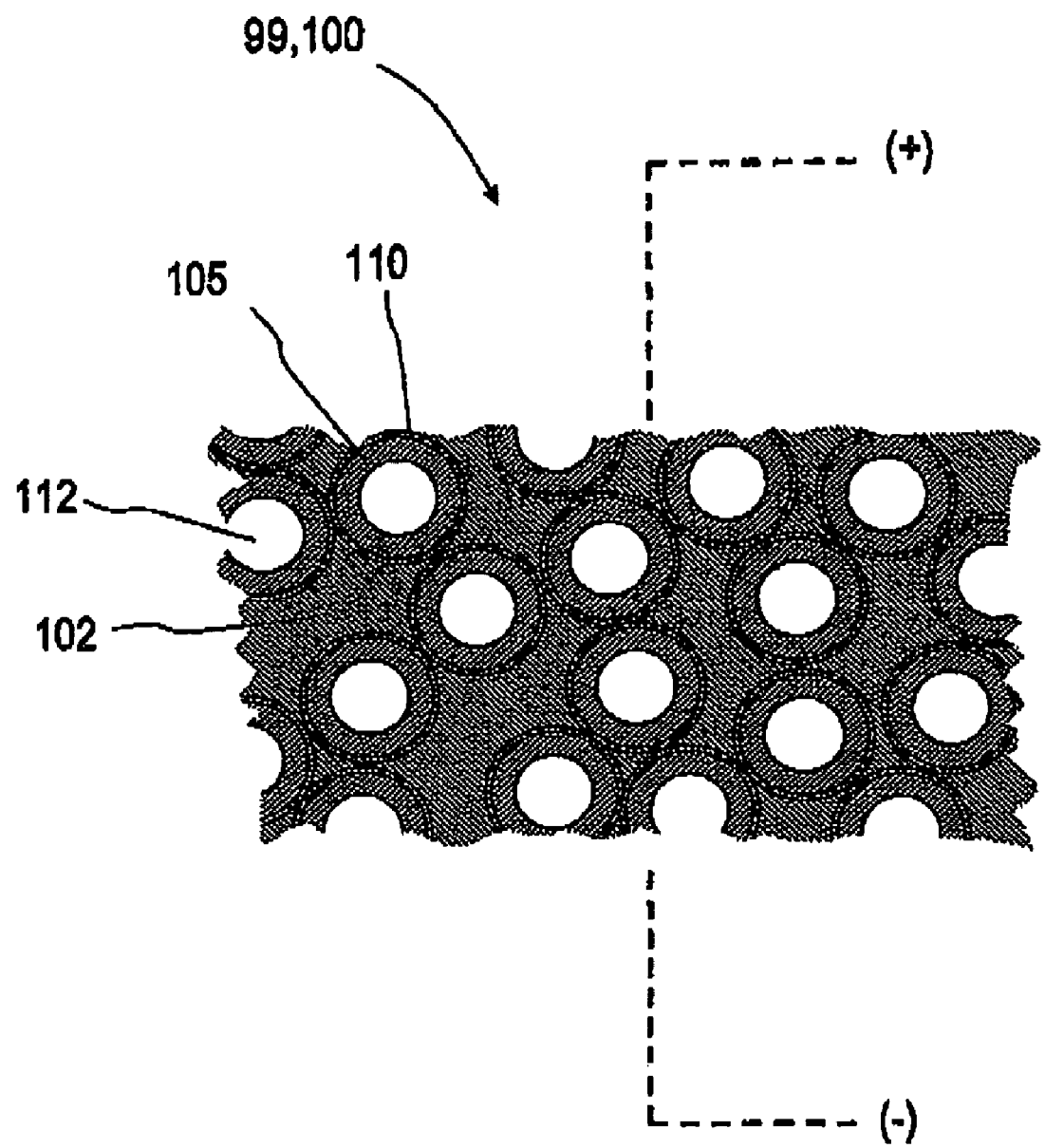
FIG. 3 is a sectional view of an exemplary polymeric PTC composite corresponding to the invention wherein a polymer component has conductively clad, low density microspheres therein.

As schematically depicted in FIG. 3, various embodiments of conductive polymer compositions exhibiting PTC properties can comprise a PTC composite 99 comprising a polymer matrix 100 including a polymer base material 102 (described below) with dispersed conductive elements (described below) which preferably have low densities and corresponding low thermal conductivity properties. More in particular, an exemplary polymeric PTC composite utilizes core-shell particles that have core 105 having a very low mass and very low thermal conductivity as in micro- and nanospheres having a nanoscale conductive coating indicated at 110. In one preferred embodiment, referring to FIG. 3, the core 105 of the conductive dispersed elements comprises glass microspheres with a hollow portion 112, but solid or porous glass microspheres or filaments fall within the scope of the invention.

In various embodiments, the polymeric PTC compositions can include conductively clad elements that have a core portion that ranges in size from about 50 nm to 250 microns across a principal axis, with a core density of less than about 2.0 g/cm³. More preferably, the density of the core portion is less than 1.0 g/cm³. Still more preferably, the density of the core portion is less than 0.5 g/cm³. In various embodiments, these densities can be the mean or bulk density of a specified sample volume or mass of elements (e.g. microspheres) and can be measured using analytical methods known in the art which can include the use of particle counting instrumentation known in the art. In various embodiments, the percentage of clad elements in the matrix having one of these cores densities can be in the range from 1 to 100%, with specific embodiments of 25, 50, 75 and 95%. In preferred embodiments, a majority of the elements have one of the three core densities.

In one embodiment, the core material can consist of hollow glass microspheres, for example, such as those available from Potters Industries, Inc., 820 Lufkin Road Apex, N.C. 27502-0298 under the name Q-CEL®. Suitable microspheres include, but are not limited to, Product Nos. 300, 6014, 6019, 6028, 6036, 6042, 6048, 5019, 5023 and 5028 available from Potters Industries. These hollow glass microspheres have mean diameters ranging from about 5 microns to 200 microns and densities that range from about 0.08 g/cm³ to about 0.50 g/cm³. Other glass, ceramic and polymer spheres and particles suitable for the invention have densities that range downward from about 1.50 to about 2.0 g/cm³. As a comparison, the apparent densities of other conductive materials commonly used in prior art polymeric PTC compositions, or could be used in a conventional manner, are as follows: Nickel powder or particles have an apparent density of 8.9 g/cm³; carbon particles have an apparent density of 2.26 g/cm³; silver particles have an apparent density of 10.5 g/cm³; tungsten particles have an apparent density of 19.3 g/cm³; copper powder or particles have an apparent density between 8.3 to 9.0 g/cm³; aluminum particles have an apparent density of 2.7 g/cm³; tantalum particles have an apparent density of 16.6 g/cm³; gold particles have an apparent density of 19.3 g/cm³; and platinum particles have an apparent density of 21.45 g/cm³. It can be seen that the dispersed conductive elements of the invention have much lower densities than prior art PTC materials.

Various embodiments of conductive polymer PTC compositions described herein can also be defined as comprising base polymers (described below) with a dispersed conductive substance. The conductive substance comprises conductively clad microspheres or other elements wherein the core of the microsphere or other element is a material that defines a very low thermal conductivity property. The metal cladding is further described below. The thermal conductivity of the core material is a measure of the ability of the material to conduct heat, determined by the rate of heat flow normally through an area in the material divided by the area and by minus the component of the temperature gradient in the direction of flow, measured in W/m-° K. (watts per meter per degree Kelvin). In one embodiment, depicted schematically in FIG. 3, the core material 105 defines a thermal conductivity of less than about 5.0 W/m-° K. Preferably, the core material 105 defines a thermal conductivity of less than about 2.0 W/m-° K. More preferably, the core material 105 defines a thermal conductivity of less than about 0.5 W/m-° K. In preferred embodiments, these values of thermal conductivity can be mean values for the quantity (e.g., mass, volume, etc.) of microspheres dispersed within the matrix or mean values for a portion of the dispersed microspheres and/or a representative sample thereof. In various embodiments, the percentage of microspheres in the matrix having one of these three core conductivities can be in the range from about 1 to 100%, with specific embodiments of 25, 50, 75 and 95%. Thermal conductivity can be measured using methods known in the art.

In various embodiments, the core material can be hollow, porous or solid elements in any microscale or nanoscale form, such as spheres, filaments, tubules, grains, flakes, powders, particles and the like that have thermal properties as described above. In a preferred embodiment, the dispersed conductive elements can comprise hollow microspheres made of a glass material in the form of soda-lime glass or borosilicate. In another embodiment, the core material can be Pyrex or any ceramic in the form of hollow microspheres or solid particles. When in the form of particles, the material can be solid or porous glass, ceramic, polymer or combination thereof but it has been found that hollow materials have suitable thermal conductivity properties as described above. The core material can have a mean diameter or other mean dimension across a principal axis ranging from about 0.5 micron to 200 microns, and more preferably between about 1 micron and 100 microns.

In one embodiment, the low density insulative core material has a conductive cladding (e.g., silver or gold) that has a thickness in range of about 0.05 nm to about 5 microns. The cladding 110 can be any suitable metallic material that can be deposited by electroplating on microspheres or other elements, or the cladding can be accomplished by a combination or electroless plating, electroplating and other cladding methods known in the art. The scope of the invention encompasses the use of any suitable electrically conductive cladding material, including but not limited to silver, gold, platinum, nickel, tin, copper, palladium, magnesium, aluminum, iron, molybdenum, tungsten, tantalum, zirconium, zinc, cobalt, chromium, carbon or combinations thereof or varying layers thereof.

Suitable conductively clad materials can comprise clad micron-dimension or nanoscale microspheres that are fabricated from a glass. In one embodiment, the core material can comprise hollow microspheres with a silver cladding that are manufactured again by Potters Industries, Inc., 820 Lufkin Road Apex, N.C. 27502-0298, under Product No. SH40033 and tradename of CONDUCT-O-FIL®. Silver clad hollow borosilicate spheres are also available as Product S-HGS-10 from Dantec Dynamics A/S, Tonsbakken 16-18, P.O. Box 121, DK-2740, Skovlunde, Denmark. The PTC composite corresponding to the invention can also be defined by density of the conductively clad particles, spheres or filaments, instead of the density of the core material described above. One hollow CONDUCT-O-FIL® product has bulk density in the range of 0.3 g/cm$^3$ to 0.4 g/cm$^3$ and a solid filament product (AgCLAD™) has a bulk density of about 1.2 g/cm$^3$. In preferred embodiments, the conductively clad elements have a bulk density of less than about 2.0 g/cm$^3$. More preferably, the bulk density of conductive element is less than 1.0 g/cm$^3$. Still more preferably, the bulk density of the conductive elements is less than 0.5 g/cm$^3$. In the embodiments described above, the glass core portion of the conductively clad elements have a resistivity of greater than about 1.0 megohm-cm. The elements, when clad with the conductive layer, define a resistivity of less than about $10^{-1}$ ohm-cm.

3. Method of Fabrication of PTC Composite with Conductive Clad Microspheres.

First, the base polymer component is mixed or compounded with the electrically conductive substance in order to uniformly disperse the conductive elements throughout the resulting matrix. Very uniform mixing of the conductive clad microspheres in the base polymer is desirable in order to create omni-directional conductive paths within the matrix as the PTC body operates. Localized separation between conductive elements as the base polymer polymerizes from a liquid into a solid can impair performance of the PTC material and also can result in internal arcing during use. The base polymer is further described below.

In one embodiment, the ratio of conductive microspheres to the total volume of the polymer matrix is greater that about 20% by volume with the base polymeric composition and optional additives making up the balance of the volume. In a more preferred embodiment, the conductive microspheres make up greater that about 40% of the volume. In ratios of conductive microspheres to total weight of the composition, the conductive microspheres can make up greater that about 10% of the total compositional weight.

In various embodiments, the base polymer component can be a crystalline or semi-crystalline polymer such as a polyolefin and more particularly a polyethylene. The base polymer also can be a copolymer of at least one olefin and one or more other monomers that can be co-polymerized with the olefin. The base polymer component also can be a polyamide, polystyrene, polyacrylonitrile, polyethylene oxide, polyacetal, thermoplastic modified celluloses, polysulfones, thermoplastic polyesters (e.g., PET), poly (ethyl acrylate), or poly(methyl methacrylate). The co-polymers also can be a nylon, a fluoropolymer such as polyvinylidene fluoride, an ethylene tetrafluoroethylene, or blends of two or more such polymers. In one preferred embodiment, the polymer base component is a high-density polyethylene, or a low-density or medium-density polyethylene, available from Dow Chemical, Union Carbide or Dupont-Mitsui Polychemicals Co., Ltd., all of which make suitable polyethylenes.

The matrix materials can be compounded or mixed using polymer processing equipment known in the art, e.g., screw or impeller type mixers or magnetic type mixers, etc. In mixing the conductive microspheres into the base polymer, it is desirable to create a highly uniform dispersal of conductive microspheres. Using any mixing or kneading apparatus known in the art, the mixing is accomplished in a mixing system configured to maintain a selected melt temperature of the base polymer.

One embodiment of a method for fabrication of conductive polymer compositions described herein includes a step for providing an inert gas atmosphere (e.g., argon gas) in which the conductive microspheres are compounded with the base polymer. For example, conductive microspheres can be mixed in a high density polyethylene at a selected temperature ranging between about 125° C. and 300° C. The protective gas atmosphere serves to substantially eliminate oxidation that may otherwise occur within the base polymer during processing. A particular advantage of this method is that the mixing or compounding step can be extended in duration—to one hour, two hours, four hours or even more of mixing time—without oxidation and the resulting degradation of the polymer composition. Further, the mixing speed of that apparatus can be slowed at any point in process to insure that conductively clad microspheres are not damaged during processing. Since the particles have a very low density and tend to float on the polymer base material during processing, the use of the inert atmosphere is very desirable in allowing for additional mixing time to insure uniform dispersal of the microspheres. In various embodiments of fabrication, the viscosity and/or other rheological properties of the composition can be measured at any point in the process to achieve one or more of the following: i) improve element dispersal; ii) control and/or optimize mixing; and iii) prevent or reduce damage to the microspheres.

In other embodiments for fabrication, the hollow conductive spheres or tubules are infused with one or more gases including without limitation, an inert gas, an anti-oxidant gas (e.g., hydrogen), a gas that is heavier than air or a gas that serves as a foaming agent. Alternatively, the hollow micro- or nanospheres can have a partial vacuum therein and can be compounded with the base polymer in a partial vacuum which can enhance the thermally non-conductive properties of the final polymer composition. These embodiments serve to further prevent or reduce oxidation within the polymer (i) during processing; and (ii) during the operational life of the polymer.

In various embodiments, the polymer matrix can carry additives known in the art that are selected to impart various chemical and physical properties to embodiments of the conductive polymer compositions. Examples of such additives include without limitation, flame retardants, anti-arcing compositions, anti-oxidizing agents (magnesium oxide or titanium oxide), anti-ozonizing agents or cross-linking agents or any combination thereof. In the fabrication process, the composition can also be treated with various cross-linking agents and processes, both chemical and radiation (e.g., gamma, UV, or E-beam irradiation), to cross-link the polymer or co-polymers of the matrix.

After embodiments of the conductive polymer PTC compositions are formulated, they can be formed or machined into various shapes and articles using one or more polymer processing and/or machining methods known in the art. For example, in one embodiment the PTC compositions can are formulated by methods described above, the compositions can be pressed into sheet material for manufacturing into various articles, such as thermistors, thermal sensors, combination thermal sensing and current-conducting devices for electrosurgical energy-delivery surfaces, and constant temperature heating devices. In the example of a thermistor, foil electrodes can be attached on either side of the PTC sheet for connection to an electrical circuit. When used as a thermal sensor or constant temperature heater, the PTC composition can be molded, extruded or otherwise formed in any suitable shape using one or more polymer processing methods known in the art (e.g., calendaring, injection molding, etc.).

One unique article that can be made from various embodiments of polymeric PTC composites described herein comprises a new class of electrosurgical energy-delivery surfaces. These surfaces can be configured to use radiofrequency (Rf) energy to perform one or more surgical procedures including, weld (including high strength welds), transect or cauterize tissue. In these and related embodiments, the PTC composites use the conductively clad, insulative microspheres to provide novel characteristics wherein the insulative microsphere component of the composite has volume percentage, density and thermal conductivity properties (described above) that disallow $I^2R$ (Joule) heating of the composite within a (i) a specified switching range and (ii) within specified electrosurgical energy delivery parameters. The specified temperature range can be between 50° C. and 200° C. In other words, such PTC composite cannot heat itself at normal electrosurgical energy power levels. Still, the surface portions of the polymer composite can respond to the temperature of engaged tissue in the specified switching range by locally switching from conductive to resistive. Of particular interest, the polymer PTC composite can locally sense tissue temperature and can switch extremely rapidly between a low base resistance value and a very high resistance value, for example, many times per second. Further, the polymer PTC composite allows for high spatial resolution, herein called pixelated resolution, for highly localized switching across a surface of the PTC material that engages tissue. No prior art thermistor materials have operating properties as described above that are needed for electrosurgical temperature-sensing and energy delivery functionality. It should be appreciated that the PTC composite described above can be used to modulate heat in any number of materials including biological tissue or non-biological materials targeted for heating.

A method of invention thus comprises (i) selecting a polymer PTC composite that defines a non-linear positive temperature coefficient of resistance (PTC) within a specified temperature range wherein the composite is configured to disallow $I^2R$ heating thereof within a specified operating range of electrical energy delivery parameters; (ii) engaging the PTC composite with a targeted material; (iii) coupling an electrical source to the PTC composite and the subject material in a series circuit to cause $I^2R$ heating of the subject material; and (iv) allowing at least portions of the PTC composite to reach the specified temperature range in response to heat conducted from the engaged subject material wherein the nonlinear PTC effect thereby modulates $I^2R$ heating in the subject material. This method allows for spatial modulation of $I^2R$ heating in the subject material, which is for example particularly useful for creating uniform heating in body tissue.

EXAMPLES

Various embodiments of the invention will now be further illustrated with reference to the following example of a polymeric composition having a highly non-linear positive temperature coefficient of resistance. However, it will be appreciated that this examples is presented for purposes of illustration and the invention is not to be limited by this specific examples or the details therein.

A quantity of silver-clad hollow glass microspheres was acquired from Potters Industries, Inc., 820 Lufkin Road Apex, N.C. 27502-0298. The microspheres are listed under Product No. SH40033 and tradename of CONDUCT-O-FIL®. Alternatively, solid or hollow glass microspheres can be acquired from Potters Industries, Inc. and clad with a gold or other conductive cladding in an electroless plating process. Estimates of the thickness of the metallic shell coating is in the range of 2 to 20 nm.

A quantity of high density polyethylene (HDPE) with 99.7% crystallinity was mixed 30% HDPE by volume to 70% clad microspheres by volume. The HDPE is available from Chevron Phillips Chemical Company LLC, 10001 Six Pines Drive, Woodlands, Tex. 77380 and has a specific gravity of about 0.90-0.96 and a glass transition temperature of approximately 120° C. The materials were placed in a Bradbury-type mixer equipped with a double screw and fluxed at 200° C. to 240° C. for a range of 2 minutes to 20 minutes. The mixing is accomplished under a protective blanket of argon gas but hydrogen gas is also possible. The PTC composition was then pelletized. The composition was treated for cross-linking purposes with a range of 250 to 450 kGy gamma irradiation. A PTC body of the material having 1.0 cm² surface area and 4.0 mm. thickness was tested which resulted in an $I_{Hold}$ of over 4.0 A at about 20° C. with high stability in its operating range.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. Further, the teachings of the invention have broad application in the electrosurgical, sensor and electronic device fields as well as other fields which will be recognized by practitioners skilled in the art.

Elements, characteristics, or acts from one embodiment can be readily recombined or substituted with one or more elements, characteristics or acts from other embodiments to form numerous additional embodiments within the scope of the invention. Hence, the scope of the present invention is not limited to the specifics of the exemplary embodiment, but is instead limited solely by the appended claims.

What is claimed is:

1. A conductive polymer composition exhibiting a positive temperature coefficient (PTC) property, the composition comprising:
    a matrix comprising at least one polymer component; and
    a plurality of conductively clad microspheres dispersed within the at least one polymer component, each conductively clad microsphere comprising an electrically conductive cladding over a core portion, wherein the plurality of core portions has a bulk density of less than about 2.0 g/cm³ and wherein the plurality of conductively clad microspheres comprises at least about 20% by volume of the composition.

2. The conductive polymer composition of claim 1, wherein the plurality of core portions has a bulk density of less than about 1.0 g/cm³.

3. The conductive polymer composition of claim 1, wherein the plurality of core portions has a bulk density of less than about 0.5 g/cm³.

4. The conductive polymer composition of claim 1, wherein the plurality of conductively clad microsoheres comprises at least about 40% by volume of the composition.

5. The conductive polymer composition of claim 1, wherein the microspheres are hollow.

6. The conductive polymer composition of claim 1, wherein the plurality of microspheres comprise at least one of microspheres, filaments, tubules, grains, flakes, particles or powder.

7. The conductive polymer composition of claim 6, wherein at least a portion of the plurality of microspheres are hollow, porous or solid.

8. The conductive polymer composition of claim 1, wherein at least a portion of the plurality of microspheres comprise at least one of a glass, a ceramic or a polymer.

9. The conductive polymer composition of claim 1, wherein a majority of the plurality of microspheres have a mean dimension across a principal axis ranging from about 0.5 micron to about 200 microns.

10. The conductive polymer composition of claim 1, wherein a majority of the plurality of microspheres have a mean dimension across a principal axis ranging from about 1 micron to about 100 microns.

11. The conductive polymer composition of claim 1, wherein the polymer component comprises at least one of a polyethylene, polyamide, polystyrene, polyacrylonitrile, polyethylene oxide, polyacetal, thermoplastic modified cellulose, polysulfone, thermoplastic polyester, poly(ethyl acrylate), poly(methyl methacrylate), nylon, polyvinytidene fluoride or ethylene tetrafluoroethylene.

12. The conductive polymer composition of claim 1, wherein a conductive cladding of the plurality of elements comprises at least one of silver, gold, platinum, nickel, tin, copper, palladium, magnesium, aluminum, iron, molybdenum, tungsten, tantalum, zirconium, zinc, cobalt, chromium or carbon.

13. A conductive polymer composition exhibiting a positive temperature coefficient (PTC) property, the composition comprising:
    a matrix comprising at least one polymer component; and
    a plurality of conductively clad glass microspheres dispersed within the at least one polymer component, each condictively clad glass microsphere comprising an electrically conductive cladding over a core portion, wherein a plurality of core portions has a mean thermal conductivity of less than about 5.0 W/m.-° K.

14. The conductive polymer composition of claim 13, wherein a thermal conductivity of each core portion is less than about 5.0 W/m-° K.

15. The conductive polymer composition of claim 13, wherein the plurality of core portions has a mean thermal conductivity of less than about 2.0 W/m-° K.

16. The conductive polymer composition of claim 13, wherein the plurality of core portions has a mean thermal conductivity of less than about 0.5 W/m-° K.

17. The conductive polymer composition of claim 13, wherein the microspheres are hollow.

18. A conductive polymer composition exhibiting a PTC property, the composition comprising:
    a matrix comprising at least one polymer component comprising at least one of polyethylene, polyamide, polystyrene, polyacrylonitrile, polyethylene oxide, polyacetal, thermoplastic modified cellulose, polysulfone, thermoplastic polyester, poly(ethyl acrylate), poly (methyl methacrylate), nylon, polyvinylidene fluoride or ethylene tetrafluoroethylene; and
    a plurality of conductively clad elements dispersed within the at least one polymer component, the plurality of elements comprising at least about 20% by volume of the composition, each element comprising an electrically conductive cladding portion over a core portion, wherein the plurality of core portions has a bulk density of less than about 2.0 g/cm³ and the cladding portion comprises at least one of silver, gold, platinum, nickel, tin, copper, palladium, magnesium, aluminum, iron, molybdenum, tungsten, tantalum, zirconium, zinc, cobalt, chromium or carbon.

19. The polymeric composition of claim 18, wherein each conductively clad element comprises an electrically conductive cladding over a core portion and each core portion has a mean resistivity of greater than about 1.0 megohm-cm.

20. The polymeric composition of claim 18, where in the plurality of conductively clad elements has a mean resistivity of less than about $10^1$ ohm-cm.

21. The polymeric composition of claim 19, wherein at least a portion of the plurality of core portions comprises at least one of a glass or a ceramic.

22. The polymeric composition of claim 19, wherein at least a portion of the plurality of core portions is hollow.

* * * * *

UNITED STATES PATENT AND TRADEMARK OFFICE
CERTIFICATE OF CORRECTION

PATENT NO.        : 7,309,849 B2                              Page 1 of 1
APPLICATION NO.   : 10/993210
DATED             : December 18, 2007
INVENTOR(S)       : Csaba Truckai et al.

It is certified that error appears in the above-identified patent and that said Letters Patent is hereby corrected as shown below:

Claim 13, Column 14, Line 17: Replace the word "condictively" with the word "conductively".

Claim 20, Column 14, Line 59: Replace the exponent "1" with the exponent "- 1"

Signed and Sealed this
Seventh Day of February, 2012

David J. Kappos
*Director of the United States Patent and Trademark Office*